United States Patent [19]

Yoakum

[11] Patent Number: 4,650,909

[45] Date of Patent: Mar. 17, 1987

[54] POLYETHYLENE GLYCOL (PEG) REAGENT

[76] Inventor: George H. Yoakum, 20304 Sandsfield Ter., Germantown, Md. 20874

[21] Appl. No.: 792,647

[22] Filed: Oct. 29, 1985

Related U.S. Application Data

[63] Continuation-in-part of Ser. No. 675,617, Nov. 28, 1984, abandoned, which is a continuation-in-part of Ser. No. 545,522, Oct. 26, 1983, abandoned.

[51] Int. Cl.$^4$ .............................................. C07C 41/36
[52] U.S. Cl. ..................................... 568/621; 568/623
[58] Field of Search ........................ 568/621, 872, 623

[56] References Cited

U.S. PATENT DOCUMENTS 2,812,360  11/1957  Mills et al. .

OTHER PUBLICATIONS

Gusev et al, CA 84: 5421g, 1976; Mater. Nawchno-Tekh. Konf. Kazon, Khim-Tekhnol. Inst. Kazan, Zavoda Org. Sint. 2nd, 1972 (pub. 1973) 117–121, (translation).
Merck Index, ninth ed., 1976, Merck & Co., Rahway, N.J., p. 984.
Kadish et al, Hybridoma, vol. 2, No. 1, 1983, pp. 87–89.
Bratanov et al, Dokl. Bolg. Akad. Nauk., 36(3) pp. 385–387, 1983.
Schaffner, W., Proc. Natl. Acad. Sci., vol. 77, p. 2163 (1980).
Rassoulzadegan et al, Nature, vol. 295, p. 257 (1982).
Sandri–Goldin, et al, Molecular and Cellular Biology, vol. 1, p. 743 (1981).

*Primary Examiner*—Howard T. Mars
*Attorney, Agent, or Firm*—John S. Roberts, Jr.

[57] ABSTRACT

A process for production of improved polyethylene glycol (PEG) is disclosed. This process overcomes the toxicity that results from using the known (and impure) PEG-fusion reagent by incorporation of a purification method that removes the toxic elements always present in PEG preparations stored above 0° C. in the presence of oxygen.

6 Claims, No Drawings

POLYETHYLENE GLYCOL (PEG) REAGENT

This is a continuation-in-part application of pending Ser. No. 675,617 filed Nov. 28, 1984 now abandoned, which is a continuation-in-part application of Ser. No. 545,522 filed Oct. 26, 1983, now abandoned.

UTILITY

The fusion grade polyethylene glycol (PEG) reagent produced by the process of this invention is a fusion reagent suitable for use in human cell genetic transfection and human/human hybridoma applications.

BACKGROUND OF THE INVENTION

There has been a long-standing need for development of serum-free culture media for various types of mammalian cells in vitro. Inherent in this development is the ability to stably move exogenous genetic information into various cell types to study the effects of homologous and non-homologous genes by the construction of stable genetic recombinant cell lines. Advantages of serum-free culture systems for the study of human somatic cell genetics include the following: (1) access to epithelial cells without the complicating factor of feeder-cells and fibroblasts; (2) the ability to study gene expression after transfection with genes that are controlled by host factors and hormones in the culture medium; (3) a reduction in experimental variation caused by the performance of serum in cell growth and gene expression; and (4) the economic benefit obtained by producing biologically active products from selected cell constructs without the need to introduce a contaminant requiring removal before the product can be used.

The polyethylene glycol (PEG) fusion method routinely used for production of mammalian cell hybrids and for transient cell expression experiments in mammalian and HeLa cells is most difficult to use as described for stable genetic transfection of human cells. See particularly Schaffner, Sandri-Goldin et al, and Rassoulzadegan et al in the Bibliography for examples of the PEG fusion method. Among other changes, this improved protocol requires the development of a new PEG fusion reagent—the subject of this invention. Removal of the toxic components of the PEG by treatment with ion exchange resins results in a reagent that is non-toxic when applied as a fusogen to normal human cells in culture. The procedure followed, and the PEG reagent used, successfully yields efficient genetic transfection of the following types of human cells: epithelial cells, mesynchemial cells, fibroblast cells, and hematopoetic cells. The types of genes used in these experiments include human virus genes linked to pSV2gpt, proviral and cellular oncogenes carried on pBR322, and human DNA libraries linked to pSV2neo.

Genetic analyses of mammalian cells have utilized cell-fusion methods to construct genetic hybrids for a number of types of tests requiring the formation of interspecies cell-cell hybrids [Pontecorvo, G; *Somatic Cell Genetics*, Vol. 1, p 397–400 (1975)], and transfer of genes carried on bacterial plasmids to mammalian cell recipients. The application of fusion technology to problems relating to human somatic cell genetics has proven difficult since many human cell types are sensitive to the cytotoxic contaminants in one of the most commonly used fusion reagents, polyethylene glycol (see Bibliography). Methods to circumvent or reduce the effect of the toxic components of polyethylene glycol (PEG) include the use of longer polymeric chain length PEG (3000 to 6000 MW) as a replacement for the more efficient membrane fusogen PEG-1000, shortened treatment times, and screening PEG lots for cytotoxic effects before selecting the least toxic reagent for application to cell fusion procedures. The present invention discloses an ion exchange resin treatment of polyethylene glycol-1000 which renders the reagent virtually non-toxic when applied as described here at 48% weight/weight (w/w) concentration to normal human fibroblast cells grown in culture. This improved fusogen provides an efficient reagent for application to human cells without causing notable cytotoxicity. This permits efficient application of fusion procedures to human cells in culture that were previously difficult or impossible to treat in vitro, and provides a reagent that will be generally useful to human somatic cell genetic analyses that involve cell membrane fusion.

GENERAL DESCRIPTION

Cell hybridization using fusion procedures is carried out using polyethylene glycol as the fusogen or fusion reagent. Equally good results are obtained with PEG reagents of molecular weight (Mr) 1000 (37% w/v) or PEG Mr 1540 (38% w/v) or PEG Mr 6000. Although the exact function that PEG performs is not known, it is believed that the PEG reagent acts as a membrane binding detergent by altering the hydrophobicity of the membrane it binds to, thus making fusion between cell membranes possible.

A standard preparation of PEG to make it suitable for use in fusion processes is described by Siraganian et al, *Methods in Enzymology*, Vol. 92, p 21 (1983) and Pontecoruo, above. Briefly, PEG 1000 Mr is autoclaved in a sterile glass bottle for 15 minutes and kept in a 56° water bath. A 35% solution (v/v) is prepared in prewarmed DMEM-HEPES (Dulbecco's Modified Eagle Medium with HEPES), and then kept at 37°. Depending on the lot of PEG or the cell lines, other concentrations of PEG may be required for optional cell fusion. Oftentimes, several dilutions of PEG are used as a serum (e.g., 30, 35, 40, 45, 50% PEG).

The above process, with some deviations, is used for animal cell fusions. Human cell fusion, however, has enjoyed limited to no success for several reasons, one of which is the PEG protocol. As has been stated above, the use of PEG is required for modification of the physical elements of a cell's membrane in order for fusion to occur. PEG made by the process described above (as well as all the modifications of that process) is suitable only for animal cell fusion. Even in animal cell fusion, the PEG protocol follows strict constraints. However, the known PEG reagents are ineffective in human/human hybridoma technology or in human cell fusions due to the toxicity of the PEG. The autoclaving step used to produce PEG fusion reagent in animal cell fusion protocols adds sufficient heat to convert some of the polyethylene glycol to aldehydes and ketones, which are membrane active toxins. These toxins lyse cells. Known procedures for using PEG sterilize the reagent to an extent only compatable with animal cells. The process described in the specific disclosure of this invention improves the PEG reagent so that human cells are now accessible using the protoplast fusion method. See the related invention of Yoakum et al, filed Oct. 25, 1983, entitled "Protoplast Fusion Method for High Frequency DNA Transfection in Human Cells," (incorporated by reference) for a description of human cell fusion and the problems attendant to the use of human cells.

Because this protocol produces a more sterile PEG reagent, the PEG produced by the process is not limited for use with protoplast fusion techniques. Processes that are capable of using PEG, but have not used it due to its toxicity, may now use PEG as the preferred reagent if sterilized according to the present invention.

In summary, the present invention is the development of a process for preparation of fusion grade PEG for human cell genetic transfection and human/human hybridoma applications. This process produces a PEG fusion reagent lacking the toxicity that present PEG reagents always contain. This toxicity limits the accessibility to recombination techniques to cell types that are much less sensitive to toxic contaminants commonly found in PEG. In practical terms, since all human cells are destroyed by the previously known PEG reagent, the PEG fusion grade reagent of the present invention allows the use of human cells.

SPECIFIC DISCLOSURE

1. Polyethylene glycol (m.w. 1000–6000) is melted by heating to 40°–42° C. This may be accomplished by heating in repeated cycles in a microwave oven until melting occurs, or by placing the 1–3 Kg bottle in a 43° C. waterbath overnight.

2. After melting, pour 300–500 ml of melted PEG into an 800 ml beaker. Test pH and adjust to pH 6.0–8.0. The preferred pH is 7.4. Add 10 grams of an ion exchange resin and mix in a 37° C. waterbath as a PEG/resin slurry for 4 hours. Mount a Buchner funnel on a vacuum flask and place a Whatman #1 filter paper over the funnel. Cover the filter paper with 10 grams of unexposed resin.

3. Slowly filter the PEG/resin slurry through the fresh resin and collect the "Fusion-Grade PEG" in the vacuum flask. This will remove toxic products from the PEG that accumulate during heating and/or storage at room temperature. Most human cells are particularly sensitive to these toxic components.

4. Place a 1 liter beaker on the balance and weigh the Fusion-Grade PEG and prepare the PEG Fusion Reagent by addition of appropriate diluent (i.e., MCDB151 nutrient medium) to yield a 48% w/w solution.

5. Filter sterilize the PEG-Fusion Reagent through 0.22u filter and store at $-20°$ C. in 100–200 ml aliquots. This is stable for at least 1 year and may be stored for several weeks at 4° C. without changing the experimental performance. Do not heat the PEG-reagent being used for human cell fusion experiments.

As indicated above, the use of an ion exchange resin is just one of the critical factors in purifying the polyethylene glycol. Ion exchange resins are well known, commonly used, and commercially available to practitioners of the art. The following resins are examples of the resins available for use in this invention, but the invention is not intended to be limited thereby. The preferred resins are Dowex mixed bed resin, Biorad AG501-8XD mixed bed resin, and QAE Sephadex 25 (Pharmacia). While the above resins are preferred, resins containing both + and − functional groups may be used either in mixed bed form or in a two-step process involving treatment with both cation-and anion-exchange resins.

Ion exchange is a method of separation used in many chemcial processes. For a general description of these processes, see Kirk-Othmer, *Encyclopedia of Chemical Technology*, Vol. 13, pp 678–705 (1981). For laboratory applications requiring extreme purity, alternating beds of cation and anion exchangers is used. In the preferred system, a mixed-bed system, hydrogen form cation resin and hydroxide form anion are intimately mixed in a single column. In the two-step process, separate beds of cation or anion resins are used. In commercial production of these resins the individual cation resins and anion resins used in the two-step process are simply combined to form the mixed bed resin exchanger. For example, Biorad sells AG1-X8 (OH$^-$) and AG50W-X8 (H$^+$) individually as well as in the mixed bed form, AG 501-X8, a one to one equivalent mixture of AG1-X8 and AG50W-X8.

The present invention includes, but is not limited to, cation exchange resins and anion exchange resins used in a two-step filtering process, or a mixed bed system which remove at least the following:

Cations: $Na^+$, $NH_4^+$, $K^+$, $Ca^{2+}$, $Mg^{2+}$, $Fe^{2+}$, $Fe^{3+}$, $Mn^{2+}$, and $Al^{3+}$.

Anions: $Cl^-$, $SO_4^{2-}$, $HPO_4^{2-}$, $HCO_3^-$, $SiO_2$, $H_3BO_3$, $NO_3^-$, and $HS^-$.

The cation exchange resins include, but are not limited to, AG50W-X8 (Biorad), 50W-X8 or HCR-W (Dow Chemical Co., "Dowex") or IRN-218 (Rohm and Haas), and their equivalents.

The anionic exchange resins include, but are not limited to, AG1-X8 (Biorad), MSA or SBR-P (Dow Chemical Co.), or IRA 900 (Rohm and Haas), and their equivalents.

The mixed bed resins include, but are not limited to, AG501-X8 (Biorad), Dowex mixed bed resin, or IRN-150 (Rohm and Haas).

All of the above resins are styrene divinylbenzene backbone resins to which + or − functional groups have been coupled.

Furthermore, the mixed bed resin system described above may optionally include 1:10 to 1:20 weight percent of dextran resin (such as QAE Sephadex) which contains a diethyl(2-hydroxypropyl)amino ethyl functional group.

The preferred embodiment of this invention involves treating melted polyethylene glycol with a mixture of Dowex mixed bed ion exchange resin and QAE-Sephadex.

Bibliography

Pontecorvo, *Somatic Cell Genetics*, Vol. 1, pp 397–400 (1975).

Rassoulzadegan et al, *Nature*, Vol. 295, p. 257 (1982).

Sandri-Goldin, et al, *Molecular and Cellular Biology*, Vol. 1, p. 743 (1981).

Schaffner, W., *Proc. Natl. Acad. Sci.*, Vol. 77, p. 2163 (1980).

EXAMPLE

The cytotoxicity of various fusogen-preparations, fusion protocols and bacterial protoplast preparations was tested by treating human fibroblasts at 80–90% confluence in 60 mm dishes followed by incubation for 3–6 days with daily medium changes for the first three days. Following the fusogen treatment and "rescue-incubation" period the cells were trypsinized, counted, and reseeded at (i) clonal density, seeding 500 and 1000 cells/60 mm dish; and (ii) mass density, $2 \times 10^5$ cells/60 mm dish. If acute cytotoxicity was observed at the time of treatment cells were seeded at approximately ten fold clonal density (10,000/60 mm dish), and mass density cultures were not attempted. The mass density cultures were fed at three-day intervals, and colony forming assay dishes were fed 24 hrs after plating and at 5–6 day intervals. To determine the net loss of viability after the procedure, colonies were fixed, stained, and counted after 9–12 days incubation at 37° C., 3.5% $CO_2$. The mass density cultures were passaged one additional time after staining the clonal density cultures to be certain that some latent toxicity not detected by the colony forming assay at day 8–12 after passage would affect the procedure. The typical colony forming efficiency (CFE) of untreated fibroblast cultures in these experiments was 12–16%. Therefore, plating values in these experiments varied by 0.04 (4%), and this was considered acceptable to validate the procedures described since less than 50% viability after normalizing the CFE of untreated control dishes to 1.0 (Table 1, legend) was not considered to be a usable procedure. The toxicity of bacterial protoplast preparations was also tested for each fusogen-preparation according to the protocol described above (Table 1).

The following methods to prepare PEG-1000 (Baker, MN 1000-1050 1M-grade) for use as a fusogen reagent were tested: (i) Method I: After weighing and autoclaving PEG the reagent was prepared by dissolving in MCDB151-medium at room temperature to yield a 48% w/w solution. Prior to the present invention, this was the preferred method of purifying the PEG and is the method described by all the authors in the Bibliography. (ii) Method II: PEG was melted by minimal heating in the microwave oven to reach 40°–45° C., weighed and mixed with MCDB151 medium stock to yield a 48% with solution. (iii) Method III: melting of PEG (as per ii) followed by treatment of PEG with Dowex ® mixed bed ion exchange resin. (iv) Method IV: treatment of melted PEG with a mixture of Dowex ® mixed bed ion exchange resin and QAE-Sephadex (PHarmacia). Method I was described by Pontecorvo and has been routinely followed since that time for most applications of PEG as a fusogen. Method II reduces the heating required to make the PEG-fusion reagent. Method III requires mixing 300 ml of melted PEG-1000 with 20 grams of Dowex ® mixed bed resin (BioRad AG501-8XD) for 4 hrs at 37° with continual agitation on a rotary shaker. PEG-preparation method IV was carried out by including 2 grams of QAE-Sephadex 25 (Pharmacia) in the batch-treated mixture of PEG and Dowex ® ion exchange resin (Method III). After batch treatment of PEG-1000 with ion exchange resins (III, IV), the slurries were filtered through a 12.5 cm diameter Whatman No. 4 filter mounted on a 14 cm Buchner funnel covered with 20 grams of unexposed Dowex ® resin. The resin treated PEG-1000 was immediately weighed, a 48% w/w solution was made by diluting the reagent with MCDB151 nutrient medium (without serum). All fusion-reagent preparations were sterilized by filtration through an 0.22 u nitrocellulose filter, divided into 200 aliquots and stored at −70° C. PEG-fusion reagents I-IV were stored at 4° C. during 1–2 week periods of frequent use.

Cell growth and cytotoxicity tests (Table 1, B): Human lung fibroblast cultures (P2-P6) were grown in MCDB104 without linoleic acid (Stock N) supplemented with $3 \times 10^{-7}$M hydrocortisone (M104) and 2% fetal bovine serum (FBS) and subcultured after reaching 80–90% confluence. The following cell growth conditions were tested for compatibility with PEG-1000 fusion procedures: (i) DMEM medium supplemented with 5% FBS; (ii) M104 with 0.2% FBS; and (iii) M104 with 2% FBS. Cell cultures had divided an average of 3–6 times in the growth medium being tested prior to treatment with PEG-1000 and subsequent passage to determine the cytotoxicity of PEG-1000.

Fusion Protocols: Two fusion protocols were tested. The fusion procedure described by Schaffner and others for bacterial protoplasts and mammalian cells (See Schaffner, Sandri-Goldin et al, and Rassoulzadegan et al in the Bibliography), was followed to test the toxicity of reagent preparation methods for human fibroblast (Protocol I). In addition, a protocol that increased the exposure of human cells to PEG-1000 by including a pre-fusion treatment with 24% PEG, followed by a 1-minute treatment with 48% w/w PEG-1000 was used to determine the extent of improvement yielded by purifying the PEG-1000 before making the fusion reagent (Protocol II). All reagents used during fusion and washing procedures were maintained at 2°–4° C. Protocol II begins with removal of medium from 80–90% confluent 60 mm culture dish of human lung fibroblasts (passage 2 to 6). Add 1.5 ml 48% PEG-1000 fusion reagent and dilute immediately with 1.5 ml dilute protoplast preparation (approximately $2 \times 10^8$ protoplasts/ml) mix and centrifuge the dishes at 850 g for 3 minutes. Remove 24% PEG aprotoplast supernatant and apply 1.5 ml 48% PEG fusion reagent to each dish. After 1 minute of treatment to initiate fusion, wash each dish 3 times with 5 ml of 4° C. MCDB151 medium. Following the wash step each culture was fed with the growth medium used before the fusion treatment 3 times at 1 hr intervals and daily for the first 3 days following treatment. The cytotoxicity of each treatment was determined by colony forming efficiency 3–6 days after the procedure. Protocol I is identical to Protocol II with the exception of the application of PEG-1000 (24% fc) at the protoplast addition step, prior to the 48% PEG-1000 fusion-treatment.

The results in Table I indicate that autoclaved PEG-1000 is cytotoxic for human fibroblasts in culture when applied in a typical fusion protocol. The toxicity of the autoclaved reagent was observed regardless of media type used and was not significantly improved by serum concentrations higher than 0.2%. Treatment of human fibroblast cultures with bacterial protoplasts and autoclaved PEG-preparations was the most cytotoxic combination tested. These conditions yielded a surviving fraction of 0.08 after the fusion treatment (Table 1).

The toxic effect of PEG-1000 prepared by methods I-IV yielded a fraction of 0.08 to 0.31 viable fibroblast cells from fusion-treated cultures when cell cultures were grown in DMEM medium before treatment. The PEG-DMEM incompatibility includes an increased sensitivity to bacterial protoplast preparations since protoplast treated cultures were 10–15% more sensitive than those cultures not treated with protoplasts during the fusion reagent toxicity tests. PEG-reagent preparation conditions III and IV (treatment with ion exchange resins) yielded greater than 50% survival for fibroblast cultures treated after growth in MCDB104-based media (Table I). PEG-1000 pretreated with ion exchange resins yielded 0.70 to 0.88 colony forming efficiency after treatment of human fibroblast cultures grown in MCDB104 with low (0.2%) or normal (2%) concentrations of serum. Although exact quantitative data were not obtained, human fibroblasts grown in RPMI 1640 with 10% FBS yielded intermediate numbers of viable cells (0.5–0.7) after fusion treatment with PEG-1000 prepared by method IV.

The results of each of these experiments show a marked improvement in the PEG of this invention over PEG of other known processes. Column E, the fraction of expanding colonies, indicates the superiority of the PEG of this invention as determined by the following: A seeding culture was formed for each kind of experiment so that about 300 colonies are formed. Within 72 hours, the colonies are treated with one of the four PEG preparations, incubated for 9–12 days, stained, and analyzed for growth. Colonies of greater than 10–15 cells were considered viable, i.e., expanding colonies. A number of 1.0 represents perfect growth.

In order to be considered a useful reagent for fusion purposes, the fraction of expanding colonies should be 45% or more. Note that DMEM (Dulbecco's Minimum Essential Medium) never worked better than 33% of the time. Other methods of animal cell fusion (see the Bibliography) are effective 40–50% for animal cells but are ineffective for human cells. The tables show graphically that the PEG fusion reagent of this invention is most effective for human cell fusion experiments.

The general application of PEG-1000 as fusion reagent for normal human cells grown in culture requires that the cytotoxic products that accumulate in PEG preparations be removed before the fusion reagent is prepared and that PEG-fusion reagents be stored frozen until 1–2 weeks before use. The cytotoxic effects of PEG-1000 fusion reagent is most evident in human cells grown in DMEM based medium (MEM-medium is similar to DMEM in this regard, data not shown). However, human fibroblasts grown in MCDB104 medium are effective recipient cultures since very low levels of toxicity are observed after treatment with 48% PEG fusion reagent prepared by pre-treatment of PEG-1000 with ion exchange resins to remove contaminants from the PEG-reagent. The resin-purified PEG-1000 provides an effective non-toxic fusogen for application to human cell fusion experiments with improved yields of viable cells. The applicability of this reagent to fusion procedures with human cells has also been demonstrated for protoplast-fusion transfection of human carcinoma cells with hepatitis b virus genes, and the transfection of proviral oncogenes into normal human bronchial epithelial cells.

Table 1 below represents experiments conducted with primary human lung fibroblasts; Table 2 is primary human bronchial epithelial cells.

TABLE I

Transfection Conditions Primary Human Lung Fibroblasts

| A PEG Preparation | | | | B Growth Media | | | C Fusion Protocol | | D | E Fraction of |
|---|---|---|---|---|---|---|---|---|---|---|
| I | II | III | IV | DMEM Fibroblast FCS | MCDB 104 0% FCS | MCDB 104 2% FCS | I | II | E. Coli (HB101) | Expanding Colonies |
| + | | | | + | | | + | | + | 0.08 |
| + | | | | + | | | + | | | 0.21 |
| + | | | | + | | | | + | + | 0.07 |
| + | | | | + | | | | + | | 0.11 |
| | + | | | + | | | + | | + | 0.11 |
| | + | | | + | | | + | | | 0.19 |
| | + | | | + | | | | + | + | 0.21 |
| | + | | | + | | | | + | | 0.18 |
| | | + | | + | | | + | | + | 0.21 |
| | | + | | + | | | + | | | 0.27 |
| | | + | | + | | | | + | + | 0.09 |
| | | + | | + | | | | + | | 0.18 |
| | | | + | + | | | + | | + | 0.24 |
| | | | + | + | | | + | | | 0.17 |
| | | | + | + | | | | + | + | 0.22 |
| | | | + | + | | | | + | | 0.31 |
| + | | | | | + | | + | | + | 0.16 |
| + | | | | | + | | + | | | 0.17 |
| + | | | | | + | | | + | + | 0.22 |
| + | | | | | + | | | + | | 0.26 |
| | + | | | | + | | + | | + | 0.41 |
| | + | | | | + | | + | | | 0.39 |
| | + | | | | + | | | + | + | 0.43 |
| | + | | | | + | | | + | | 0.36 |
| | | + | | | + | | + | | + | 0.81 |
| | | + | | | + | | + | | | 0.86 |
| | | + | | | + | | | + | + | 0.83 |
| | | + | | | + | | | + | | 0.91 |
| | | | + | | + | | + | | + | 0.94 |
| | | | + | | + | | + | | | 0.93 |
| | | | + | | + | | | + | + | 0.87 |
| | | | + | | + | | | + | | 0.89 |
| + | | | | | | + | + | | + | 0.17 |
| + | | | | | | + | + | | | 0.26 |
| + | | | | | | + | | + | + | 0.22 |
| + | | | | | | + | | + | | 0.24 |
| | + | | | | | + | + | | + | 0.58 |
| | + | | | | | + | + | | | 0.66 |
| | + | | | | | + | | + | + | 0.52 |
| | + | | | | | + | | + | | 0.71 |
| | | + | | | | + | + | | + | 0.87 |
| | | + | | | | + | + | | | 0.81 |
| | | + | | | | + | | + | + | 0.80 |
| | | + | | | | + | | + | | 0.84 |
| | | | + | | | + | + | | + | 0.89 |
| | | | + | | | + | + | | | 0.96 |
| | | | + | | | + | | + | + | 0.91 |

TABLE I-continued

Transfection Conditions Primary Human Lung Fibroblasts

| A PEG Preparation | | | | B Growth Media | | | C Fusion Protocol | | D E. Coli (HB101) | E Fraction of Expanding Colonies |
|---|---|---|---|---|---|---|---|---|---|---|
| I | II | III | IV | DMEM Fibroblast FCS | MCDB 104 0% FCS | MCDB 104 2% FCS | I | II | | |
| | | | + | | | + | | + | + | 0.93 |

TABLE II

Transfection Conditions Primary Bronchial Epithelial Cells

| A PEG Preparation | | | | B Growth Medium LHC4 (Serum Free) | C Fusion Protocol | | D E. Coli (HB101) | E Fraction of Expanding Colonies |
|---|---|---|---|---|---|---|---|---|
| I | II | III | IV | | I | II | | |
| + | | | | + | + | | + | 0.09 |
| + | | | | + | + | | | 0.08 |
| + | | | | + | | + | + | 0.11 |
| + | | | | + | | + | | 0.13 |
| | + | | | + | + | | + | 0.29 |
| | + | | | + | + | | | 0.21 |
| | + | | | + | | + | + | 0.28 |
| | + | | | + | | + | | 0.24 |
| | | + | | + | + | | + | 0.83 |
| | | + | | + | + | | | 0.88 |
| | | + | | + | | + | + | 0.89 |
| | | + | | + | | + | | 0.91 |
| | | | + | + | + | | + | 0.84 |
| | | | + | + | + | | | 0.93 |
| | | | + | + | | + | + | 0.86 |
| | | | + | + | | + | − | 0.85 |

I claim:

1. A process for the production of polyethylene glycol (PEG) molecular weight, 1000–6000 for human cell genetic transfection comprising
   melting PEG;
   adding a resin to said PEG to form a PEG/resin slurry at a pH of about 7.4, said resin consisting of cationic and anionic resins selected from the group consisting of a mixed bed resin containing a styrene-divinyl benzene backbone, a cross-linked dextran containing a diethyl (2-hydroxypropyl)amino ethyl functional group, and mixtures thereof;
   filtering the PEG/resin slurry through fresh mixed bed resin to obtain the improved PEG.

2. The process of claim 1 wherein the resin is said mixed bed divinylbenzene resin in combination with said dextran resin with an amino functional group.

3. The process in claim 1 wherein said improved PEG is 1000 molecular weight and a melting point of about 42° C.

4. A fusion grade reagent suitable for use in human cell fusion produced by the process comprising
   melting polyethylene glycol (PEG) molecular weight, 1000–6000
   adding a resin to form a PEG/resin slurry at a pH of about 7.4, said resin consisting of cationic and anionic resins selected from the group consisting of a mixed bed resin containing a styrene-divinyl benzene backbone, a cross-linked dextran containing a diethyl (2-hydroxypropyl)-amino ethyl functional group, and mixtures thereof;
   filtering the PEG/resin slurry through fresh mixed bed resin to obtain the improved PEG.

5. The fusion grade reagent in claim 4 wherein said resin is said mixed bed divinylbenzene resin in combination with said dextran resin with an amino functional group.

6. The reagent of claim 4 wherein said fusion grade reagent is 1000 molecular weight polyethylene glycol with a melting point of about 42° C.

* * * * *